United States Patent [19]
Flinsenberg et al.

[11] 4,444,500
[45] Apr. 24, 1984

[54] DEVICE FOR MEASURING PARTICLES IN A FLUID

[76] Inventors: Harry J. Flinsenberg; Jan P. van Dijke, both of Eindhoven University of Technology, Department of Electrical Engineering, P.O. Box 513, 5600 MB Eindhoven, Netherlands

[21] Appl. No.: 273,187

[22] Filed: Jun. 12, 1981

[30] Foreign Application Priority Data

Jun. 13, 1980 [NL] Netherlands .......................... 8003429

[51] Int. Cl.³ ............................................ G01N 15/02
[52] U.S. Cl. ..................................................... 356/336
[58] Field of Search ........................................ 356/336

[56] References Cited

U.S. PATENT DOCUMENTS

| | | | |
|---|---|---|---|
| 4,140,395 | 2/1979 | Krickebaum | 356/336 |
| 4,179,218 | 12/1979 | Evdmann et al. | 356/336 |
| 4,329,054 | 5/1982 | Bachalo | 356/336 |
| 4,348,111 | 9/1982 | Goulas et al. | 356/336 |

*Primary Examiner*—Bruce Y. Arnold
*Attorney, Agent, or Firm*—Cushman, Darby & Cushman

[57] ABSTRACT

An improved particle analyzer in which a broad measuring beam and a narrower, parallel triggering beam of electromagnetic radiation are sent through a stream of particles. The light scattered by the particles is detected and recorded. At the recording a coincidence signal caused by scattered radiation from the triggering beam ensures that only those particles are counted which have traversed the triggering beam and for this reason the core of the measuring beam. The improvement consists in the use of a triggering beam outside of the broader measuring beam. According to a further improvement the shape of the measuring beam is smaller in the flow direction of the particles than in a direction perpendicular thereto. In this way the analyzer is better suited for the use of one color laser light and higher particle velocities.

7 Claims, 5 Drawing Figures

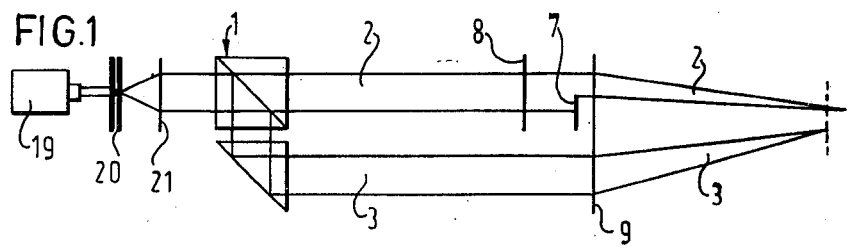
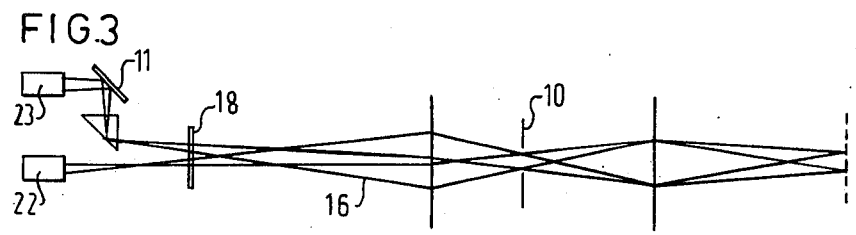
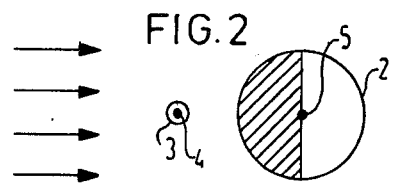
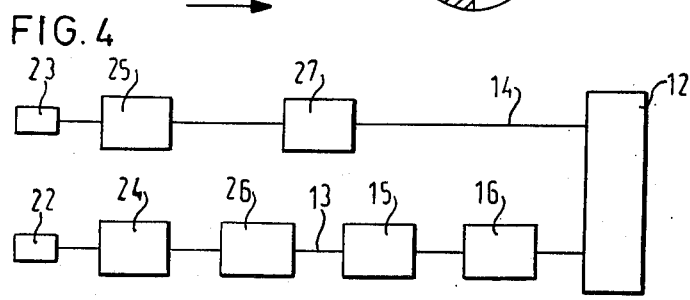
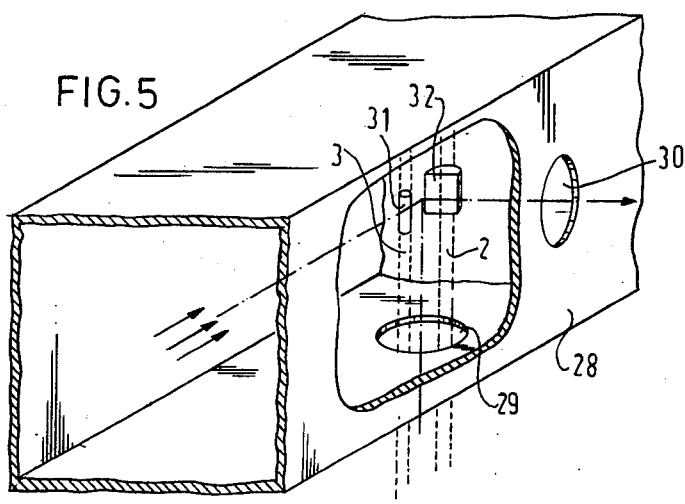

DEVICE FOR MEASURING PARTICLES IN A FLUID

The invention relates to a method for measuring the number and size of particles in a streaming fluid with the aid of a laser beam, which beam is split into two separate beams which are directed transversely through the fluid, while the radiation, scattered by the particles in the beam, is caught, detected and recorded. The invention relates to a device for application of this method as well.

From the U.S. Pat. No. 4,179,218, equipment of this general is known where two equal mutually crossing laser beams are used, in this case the particles are detected by the scattered radiation from the area where the two beams intersect one another. This known equipment is meant to measure the scattered radiation from those particles which are in the centre of the two mutually crossing and overlapping beams, in this way, only the particles are counted which are moving through that part of the space where the two different laser beams are intersecting. A disadvantage of this method is that the intensity of the laser beam varies according to a Gaussian distribution, (spatial bell curve), so that the intensity of the beam is highest in the centre, therefore the intensity of the radiation, scattered by the particles which are moving through this central area, is higher than from elsewhere. It appears that due to the variation in intensity of the scattered light from particles in different locations of the area where the laser beams are intersecting, insufficient information is obtained about the actual size of the different particles.

It is possible to solve this problem by trying to provide a spatial distribution of the intensity of the laser beam having rectangular shape. In practice this has lead however to the following conclusions:

it appeared to be necessary to use in the optics for projection, lenses of an extremely high quality, this is of course very expensive.

after the installation of achromatic lenses, it appeared that the maximum result is an intensity profile in the beam showing a variation of 50 in the top and 25% variation in the flanks. This is a consequence of significant interference and diffraction effects occurring in the focal area and also due to imperfections in the lenses.

For this reason, it appeared to be almost impossible to use a laser beam with an optical intensity profile of a rectangular shape.

The present invention has for its object the removal of the influence of the flanks of the Gaussian intensity profile by a method which differs strongly from the method described in the earlier mentioned U.S. Pat. No. 4,179,218.

According to the invention one should a. divide the laser beam into two different incident beams such that, depending on the direction of the stream of the fluid, one of those is preceded or followed by the second beam the second being narrower than the first one and both running principally parallel such that the centre lines of either of the incident beams be in one plane; b. detect independently and convert into a pulse the light from the first incident beam scattered by the traversing particles and radiation of the second beam being also scattered, by the particles; c. use the pulse signal due to the particles traversing the second beam as a coincidence signal for the pulse occuring by the interaction of the same particles with the first laser beam.

A new principle in the presently suggested method and equipment is the use of an optical signal working cooperatively with coincidence equipment.

Although the new method for counting the particles in a specific measuring volume works perfectly, it is still possible that there remains some "cross talk" of the measuring beam on the triggering beam. In the following, the second narrow beam will be indicated as triggering beam. Due to very small imperfections in the measuring beam, some scattered light intensity may reach the edge of the triggering beam very closely, so particles which have not traversed the triggering beam may however give rise to a scattering signal which will be interpreted by the detection equipment as radiation scattered by particles having indeed passed the triggering beam.

In principle both measuring beam and triggering beam possess a circular cross section. Preferably it is possible to get rid of the "cross talk" of the measuring beam on the triggering beam by selecting the proper optical components such that the cross section of the beam obtains a shape having smaller dimensions in the direction of the stream than in the perpendicular direction. One may think, for instance, of an elliptical cross-section of the measuring beam instead of a circular one. A further advantage of this suggested alteration of the cross section of the measuring beam is the adjustability of the measuring instrument to higher velocities of the fluid which contains the particles to be detected in this way. Indeed it is possible to bring the triggering beam closer to the centre line of the measuring beam.

An altered cross section of the measuring beam which is most simply arrived at, is a measuring beam having the shape of a half straight circular cylinder. This half straight circular cylinder shape is most easily realized by means of a diaphragm or an edge such as an optical knife edge.

An important property of the presently suggested equipment is that the distance between triggering beam and measuring beam can be focussed at a variable distance by adjusting one or more lenses. In this way the instrument can be adjusted to different velocity ranges of the fluid stream containing particles to be detected, by which the range of applicability is greatly extended. In a practical case with a fluid stream velocity of about 200 meters per second, the triggering beam will have a diameter of ¼ to 3 mm, while the diameter of the measuring beam will lie between 0.5 and 5 mm, and varies the distance between the centre line of the triggering beam and measuring beam between 0.5 and 6 mm.

Preferentially it is possible to set up the equipment to the height by accomodation of an adjustable diaphragm into the optical projection system, and therefore the specific measuring volume formed by the triggering and measuring beam, from which the scattered light is being measured. In this way, it will be possible to select a suitable measuring volume if too many or too little particles are being counted per unit of time.

In many cases it is necessary to exclude the emitted light by for instance the flames, in the case of measurements on smoke or, if one is intending to determine the amount of dust particles in the case of a MHD plasma, by means of an interference filter of for instance $\delta\lambda = 0.1$ nanometer. This interference filter has to be placed in front of the final separation system which has the function to separate the triggering from the measuring beam, before they are detected by photo multiplier tubes.

In order to improve the measuring range of different particle sizes, in the detection equipment for the measuring beam preferentially an amplifier with a high dynamic range (0.5 m V–20 V) and a large band width (0–2000 kHz) is placed. In such a case it will be possible to detect particles of sizes between 0.05 and 150 micron within only one measuring range. The electronic pulses are directly related to the particle sizes.

In order to eliminate noise and other background effects, a voltage comparator is applied in the detection system for the scattered radiation of the triggering beam.

A multichannel analyzer, MCA, such as the commercially available MCA Le Croy gv T 3001 can be made fit for the circuitry which registrates the signals from the triggering beam by subsequent accomodation of a monostable multivibrator being adjusted to a delay time of for instance 4 microseconds in a second monostable multivibrator adjusted to a delay time of 6 microseconds. If the gas velocity, and therewith of course also the particle velocity amounts about 200 meter per second, this will lead to the following result.

A particle which traverses the triggering beam will lead to a period of 4 microseconds during which the counting system of the multichannel analyzer is dead. This dead period now is initiated by the scattering of the radiation on the particle. During this period 4 microseconds this particle will be travelling the distance from the triggering beam to the measuring beam. By the time it has reached the centreline of the measuring beam, which preferentially has a cross section of the shape of a half straight circular cylinder, the particle that has to be detected will in theory almost immediately give the maximum scattering of the light. In practice however there is some time delay of about one microsecond before the maximum amount of scattered light is dissipated, in order to make sure that the maximum amount of scattered light is detected in the measuring beam, one should take 6 microseconds for the period during which the electronics is blind.

Excellent results have been obtained with a 5 W argon-ion laser ($\lambda = 515.4$ nanometer).

If the measurement is conducted on a gas which is radiating a lot of light as it occurs in a MHD blowdown experiment, it is best to measure at an angle of approximately 90° with the direction of the velocity of the gas, although scattering of light by particles is greatest in the direction in which particles are moving and smallest in the perpendicular direction. In this way disturbance by the light from the experiment is prevented.

In principle the invention is applicable with all kinds of radiation sources which have a more or less gaussian intensity distribution, herewith is meant that the highest intensity in the centre of the beam deviates significantly from the intensity at the edge of the beam and nevertheless, a relatively large area with maximum intensity is present. Of course, the invention can also be applied with electromagnetic radiation of other frequences. Besides application in the aforementioned MHD experiment, the invention is also very well applicable in smoke gas channels occuring in apparatus fired with coal.

In the drawings:

FIG. 1: a schematic view of the path of the laser beams;

FIG. 2: a cross section of the two beams at the location where the measurement is conducted;

FIG. 3: a schematic view of the optics for the detection along with the radiation path;

FIG. 4: a schematic view of the electronic part connected to the detection optics; and FIG. 5: a spatial view of the measuring system in the main channel where the measurement is done.

In FIG. 1, the laserlight source is indicated by 19, which source is equipped with a filter 20. The light emitted by the laser 19 is converted into a parallel beam by means of the lens 21. This parallel beam is subsequently split into two beams, 2 and 3, by means of a separation module comprising a double prism and a second one to deflect the beam by an angle of 90°. The upper beam 2 subsequently traverses a lens 8 after which a sharp edge 7 as truly absorbs half of this beam. This "halved" measuring beam and the lower triggering beam consequently traverse a converging lens 9. Due to the difference in refraction at the different locations of the optical system, the triggering beam and the "halved" measuring beam will be focussed at different locations behind one another. These locations can be altered or adjusted in this case by means of a adjustable lens 8 placed in one of both beams, it is also possible in this way by a proper adjustment of the locations of both focal points to select the desired ratio of the diameters of the triggering beam 3 and the measuring beam 2. (In FIG. 2 the hatched area indicates the cross section of that part of the main beam which is absorbed by the sharp edge 7). In the system of lenses, the lens 9 is placed beyond a prism (not indicated in the figure) which is traversed by both beams 2 and 3 and making detection of the scattered radiation at angle 90° feasible. The detection equipment, shown in FIG. 3, is in fact mounted parallel to the laser beam equipment shown in FIG. 1. Installation on top of one another of the laser beam equipment and the detection equipment is sometimes advantageous, since in such a case only on one side of the main channel space for apparatus will be required.

In FIG. 2 the points indicated with 4 and 5 show the centrelines of triggering beam 3 and the "halved" measuring beam 2 respectively, the hatched left part of the measuring beam indicates that part of the beam which has been taken away by the optical edge 7 in FIG. 2.

The distance between the points 4 and 5 in this case equals 1.5 mm, while the diameters of the triggering beam and measuring beam are taken 0,5 and 3 mm respectively. The direction of the gasstream with dust particles is indicated by arrows at the left hand side.

It should be mentioned that during application of a second beam following the measuring beam, the non hatched part of the measuring beam as it is shown in this case should be absorbed by the optical edge 7.

In FIG. 3 it is explained how the scattered light from the particles traversing triggering beam 3 and measuring beam 2 is lead to the two photo multiplier tubes (to be abbreviated as PMT 22 and 23) by means of an optical projection system 16. The PMT 22 in this case is the input channel for the signal of the triggering beam 3 while the PMT 23 receives the signal from the measuring beam 2. In the optical project system 16 an adjustable diaphragm 10 is accommodated in order to control the final counting rate. An interference filter 18 is placed in front of the separation system 11 and has the function to separate the scattered intensities of both beams 2 and 3. The separation system 11 comprises a 90° prism and a mirror. The PMT's 22 and 23 are shown in the block or line diagram given in FIG. 4.

In FIG. 4 the "trigger" PMT 22 in the detection system for the triggering beam gives a signal which, with the aid in the monostable multivibrator 15 (=delay time) and the monostable multivibrator 16 (=gate pulse), causes a gate signal to the MCA. One receives the proper trigger by adjusting the multivibrator 15 in such a way that the gate pulse appears at the same moment as the measuring pulse from the detection circuit 14 of the measuring beam. In both detection circuits 13 and 14, also two emission followers 25 and 24 are accommodated while the circuit 13 comprises a voltage comparator 26 and the circuit 14 an amplifier 27. The circuits 14 and 15 are both connected to the MCA indicated with 12.

In FIG. 5, a flow channel is indicated with 28, a flow of gas loaded with dust particles is running from left to right in the plane of the drawing. In the flow channel 28, a window 29 is mounted on the bottom part through which the triggering beam 3 and the measuring beam 2 are entered. At the right hand side of the flow channel 28, a detection window 30 is mounted beyond which the parallel detection optics and coincidence equipment, shown in FIGS. 3 and 4, are placed.

The thick sections of triggering beam 3 and measuring beam 2, indicated in the figure, are those parts of the beams where the traversing particles are being counted. The height of this thick indicated cylinder 31 of triggering beam 3 and the half circular cylinder 32 of the measuring beam is determined by the diaphragm 10 as shown in FIG. 3. The diaphragm 10 determines the height and herewith the volume in which particles can be counted. One half of the measuring beam 2 has been halved by the optical edge 7, shown in FIG. 1. The directions given by the MCA indicated with 12 in FIG. 4 and the further electronic instruments can be calibrated by methods known per se in relation to model aerosols with well defined particle sizes, and concentrations.

For other fluids it is possible to perform the calibration by using mono dispersive soles which, during the calibration procedure, flow through the measuring duct with known particle concentration and velocity.

We claim:

1. In a method for electro-optically measuring the number and size of particles in a streaming fluid with the aid of a laser beam by splitting this beam into two different beams, both running through the fluid, and by subsequently detecting and recording the scattered radiation from the particle traversing the beams, the improvement wherein
   a. the laser beam is divided into a first beam and a second beam such that, with respect to the direction of the stream of the fluid, the second beam is preceded by a first beam, which first beam is more narrow in cross-section than the second beam and wherein both beams are aligned almost parallel such that the centrelines of the beams are in one plane;
   b. the light scattered by a particle in the first beam and the light scattered by said particle when it is in the second beam is detected and is separately converted into pulses;
   c. the pulse caused by a particle traversing the first beam is used as a timing signal to time the detection of the scattered light in said second beam so that the particle is in that special portion of the second beam which has a relatively constant spatial intensity distribution.

2. In an electro-optical system for measuring number and size of particles in a streaming fluid comprising: a source for laser light; means to divide the radiation beam from said source into two beams consisting of a first beam and a second beam; means to conduct said beams through a streaming fluid which may contain particles; and detection equipment to detect and record the radiation scattered by the particles, the improvement wherein
   a. optical means are provided which can divide the radiation beam into said two beams, said optical means including a double prism, a second prism to deflect the second beam, and a set of adjustable lenses, said optical means so designed and so placed that during operation
      (i) both said first beam and said second beam are almost parallel and their centre lines are in one plane;
      (ii) said one plane is directed perpendicular to the streaming fluid; and
      (iii) the first beam has a narrower cross-section than the second beam;
   b. mechanical means are provided comprising:
      (i) a fluid-flow-channel;
      (ii) a window in the wall of said channel perpendicular to the centrelines of both beams;
      (iii) a second window which is mounted in said wall nearly parallel to the plane formed by the centrelines of the beams;
   c. detecting means are provided to convert light scattered from each of the beams through the second window into separate electrical pulses; and
   d. an electronic circuit is provided to convert said electrical pulses into registerable signals, said electronic circuit comprising
      (i) a multi channel analyzer unit connected with
      (ii) a pulse channel from the detecting means corresponding with the first beam and
      (iii) a pulse channel from the detecting means corresponding with the second beam, which latter pulse channel comprises means to time the detection by the analyser unit of light scattered by said second beam.

3. A system as in claim 2 wherein the cross-section of the first beam has the shape of a half circle, showing the midline towards the second beam.

4. A system as in claim 3 including an optical knife or diaphragm for determining the shape of the first beam.

5. A system as in any one of claims 2, 3 or 4 wherein said source is an argon gas laser and wherein the two beams are dimensioned in such a way that, with fluid flow velocity of about 200 meters per second, the second beam has a diameter of ¼ to 3 mm, the first beam a diameter of 0.5 to 5 mm and the distance between the second beam and the centreline of the first beam is 0.5 to 6 mm, said system including a separation system for separating the scattered intensities of both beams for the final pulse detection and an interference filter.

6. A system as in any one of claims 2, 3 or 4 including an optical projection system for the scattered light, said projection system including an adjustable diaphragm.

7. A system as in any one of claims 2, 3 or 4 wherein the recorder is a multi-channel analyser connected to both the detection circuits, which circuits comprise:
   (i) for the circuit connected to the detecting means of the first beam, an amplifier with a range of 0.5 mV to 20 V and a bandwidth of 0–2000 kHz; and
   (ii) for the circuit connected to the detecting means of the second beam, a voltage comparator and two monostable multivibrators to settle delay time and to act as a gate, respectively.

* * * * *